US010598589B2

United States Patent
Choi et al.

(10) Patent No.: US 10,598,589 B2
(45) Date of Patent: Mar. 24, 2020

(54) OPTICAL PROBE BASED ON THIN-FILM INTERFERENCE

(71) Applicant: Research & Business Foundation Sungkyunkwan University, Suwon-si (KR)

(72) Inventors: Myunghwan Choi, Suwon-si (KR); YongJae Jo, Suwon-si (KR); Junhwan Kwon, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 16/359,006

(22) Filed: Mar. 20, 2019

(65) Prior Publication Data

US 2019/0293549 A1    Sep. 26, 2019

(30) Foreign Application Priority Data

Mar. 20, 2018   (KR) ........................ 10-2018-0031980

(51) Int. Cl.
   *G01N 21/25*   (2006.01)
   *G01J 3/45*    (2006.01)
   *G01N 33/543*  (2006.01)
   *G01N 21/27*   (2006.01)

(52) U.S. Cl.
   CPC .............. *G01N 21/255* (2013.01); *G01J 3/45* (2013.01); *G01N 21/272* (2013.01); *G01N 33/54313* (2013.01)

(58) Field of Classification Search
   CPC ........ G01J 3/45; G01N 21/45; G01N 21/8422
   See application file for complete search history.

(56) References Cited

U.S. PATENT DOCUMENTS

| 8,158,374 | B1* | 4/2012 | He | G01N 33/6896 |
| | | | | 435/7.1 |
| 2005/0019842 | A1* | 1/2005 | Prober | B82Y 20/00 |
| | | | | 435/7.9 |
| 2011/0019186 | A1* | 1/2011 | Himmelhaus | G01N 21/648 |
| | | | | 356/317 |
| 2011/0256528 | A1* | 10/2011 | Poetter | G01N 33/54313 |
| | | | | 435/5 |

FOREIGN PATENT DOCUMENTS

KR    10-2017-0075221 A    7/2017

OTHER PUBLICATIONS

Jo, Yongjae et al., "Reflectophore: microsphere-based reflective optical probe", 39th Annual International Conference of the IEEE Engineering in Medicine and Biology Society, Jul. 11-Jul. 15, 2017 (3 pages in English).

* cited by examiner

*Primary Examiner* — Jonathan M Hansen

(74) *Attorney, Agent, or Firm* — NSIP Law

(57) ABSTRACT

The present disclosure relates to a method of analysis by an optical marker, including: irradiating a broadband light source onto a spherical dielectric material; measuring an interference spectrum of reflected light from the spherical dielectric material; and analyzing the reflected light using thin-film interference theory.

13 Claims, 16 Drawing Sheets

OPTICAL PROBE BASED ON THIN-FILM INTERFERENCE

CROSS REFERENCE TO RELATED APPLICATIONS

This application claims the benefit under 35 USC § 119(a) of Korean Patent Application No. 10-2018-0031980, filed on Mar. 20, 2018, in the Korean Intellectual Property Office, the entire disclosure of which is incorporated herein by reference for all purposes.

TECHNICAL FIELD

The present disclosure relates to an optical probe based on thin-film interference which occurs in a spherical dielectric material.

BACKGROUND OF THE INVENTION

Optical markers capable of labeling different individuals in complex tissue are highly utilized in biological research. Particularly, cells of the same type express different genes, and, thus, it is useful to observe each type of cell in monitoring the metastasis of cancer or the development of life. A fluorescence marker which is one of the most widely used optical markers is easy to use. However, due to the occurrence of photobleaching, a signal fades as time goes on, and, thus, the fluorescence marker cannot trace a fluorescence-labeled individual for a long time. Further, the fluorescence marker has a relatively broad range of emission spectrum, and, thus, the number of colors which can be used for labeling at the same time is limited to 3 to 5. Therefore, the fluorescence marker cannot label each individual in hundreds or thousands of cells at the same time.

Korean Patent Laid-open Publication No. 2017-0075221 which is the background technology of the present disclosure relates to an optical marker for a biosensor, an optical biosensor including the optical marker, and a method of manufacturing an optical marker for a biosensor. However, Korean Patent Laid-open Publication No. 2017-0075221 relates to an optical marker for a biosensor including an analyte-sensing substance selectively conjugated to a target analyte, but does not describe a technology capable of analyzing the sizes of hundreds of micromaterials at the same time.

DISCLOSURE OF THE INVENTION

Problems to be Solved by the Invention

The present disclosure is conceived to solve the above-described problem of the conventional technology and provides a method of analysis by an optical marker.

However, problems to be solved by the present disclosure are not limited to the above-described problems. There may be other problems to be solved by the present disclosure.

Means for Solving the Problems

As a technical means for solving the above-described technical problems, a first aspect of the present disclosure provides a method of analysis by an optical marker, including: irradiating a broadband light source onto a spherical dielectric material; measuring an interference spectrum of reflected light from the spherical dielectric material; and analyzing the reflected light using the thin-film interference theory.

According to an embodiment of the present disclosure, the method may further include, before the analyzing of the reflected light using the thin-film interference theory, normalizing the broadband light source and the reflected light, but may not be limited thereto.

According to an embodiment of the present disclosure, the analyzing of the reflected light using the thin-film interference theory may include comparing a function of an analyzed intensity R of the reflected light according to the following Equation 1 to Equation 4 with an actually measured intensity R of the reflected light, but may not be limited thereto.

$$M = \begin{pmatrix} M_{11} & M_{12} \\ M_{21} & M_{22} \end{pmatrix} = J_0^{-1} \left( \prod_{i=1}^{m} H_i \right) J_m \quad \text{[Equation 1]}$$

In the above Equation 1, when the spherical dielectric material is formed of m number of layers, J is represented by the following Equation 2, $$J_i = \begin{pmatrix} s_i & s_i \\ t_i & -t_i \end{pmatrix}, i = 1, \ldots, m+1 \quad \text{[Equation 2]}$$

H is represented by the following Equation 3, and $$H_i = \begin{pmatrix} \cos(kn_id_i\cos\theta_i) & i\sin(kn_id_i\cos\theta_i)\frac{s_i}{t_i} \\ i\sin(kn_id_i\cos\theta_i)\frac{t_i}{s_i} & \cos(kn_id_i\cos\theta_i) \end{pmatrix}, i = 1, \ldots, m \quad \text{[Equation 3]}$$

in the above Equations 1, 2, and 3, $d_i$ represents the thickness of an ith thin film of the spherical dielectric material, $\theta_i$ represents the degree of an incident angle of the broadband light source, $n_i$ represents the refractive index of the ith thin film of the spherical dielectric material, and in a transverse electric field mode, $s_i$ is 1, $t_i$ is $n_i \cos \theta_i$, and k is represented by $$\frac{2\pi}{\lambda},$$

and in a transverse magnetic field, $s_i$ is $\cos \theta_i$ and $t_i$ is $n_i$, but may not be limited thereto.

$$R = \left| \frac{M_{21}}{M_{11}} \right|^2 \quad \text{[Equation 4]}$$

In the above Equation 4, R represents the intensity of the reflected light.

According to an embodiment of the present disclosure, the spherical dielectric material may have a diameter of from 0.1 μm to 500 μm, but may not be limited thereto.

According to an embodiment of the present disclosure, the spherical dielectric material may include soft materials including a solid polymer, hydrogel, liposome, and combinations thereof, or gas-based materials including aerogel, but may not be limited thereto.

According to an embodiment of the present disclosure, the spherical dielectric material may include one material layer or two or more material layers, but may not be limited thereto.

According to an embodiment of the present disclosure, the spherical dielectric material may have a surface coated with a material having binding specificity, but may not be limited thereto.

According to an embodiment of the present disclosure, the spherical dielectric material may have stimuli-responsive reactivity sensitivity and thus may vary in size or internal refractive index depending on chemical or physical conditions, but may not be limited thereto.

According to an embodiment of the present disclosure, the spherical dielectric material may include a spherical dielectric material of multiple layers which are different from each other in thickness or internal refractive index, but may not be limited thereto.

According to an embodiment of the present disclosure, the broadband light source may have a wavelength with a bandwidth of from 20 nm to 2,000 nm, but may not be limited thereto.

According to an embodiment of the present disclosure, the measuring of the interference spectrum of the reflected light may be performed by a spectroscope or an acoustic-optic tunable filter, but may not be limited thereto.

According to an embodiment of the present disclosure, the interference spectrum may be measured by selectively collecting only an optical focus signal of reflected light reflected from the center of the spherical dielectric material with a confocal optical system, but may not be limited thereto.

The above-described aspects are provided by way of illustration only and should not be construed as liming the present disclosure. Besides the above-described examples, there may be additional examples described in the accompanying drawings and the detailed description.

Effects of the Invention

According to the above-described aspects of the present disclosure, in a method of analysis by an optical marker of the present disclosure, when the size of a spherical dielectric material is measured repeatedly for analysis, the standard deviation in the measurement is less than 2 nm, which means that the accuracy is high. For this reason, when there are markers different in size up to about 1 μm, the sizes of 20 or more spherical dielectric materials can be analyzed at the same time. Further, when the sizes of spherical dielectric materials with a difference in size of more than 1 μm are analyzed, thousands or more of the spherical dielectric materials can be analyzed at the same time. The conventional fluorescence marker has the disadvantage that it can label only 3 to 5 subjects at the same time. The method of the present disclosure is a method to overcome the disadvantage of the conventional fluorescence marker. Since it is possible to analyze multiple subjects at the same time, it is possible to trace and observe individual cells in a cell aggregate. Particularly, the method of the present disclosure can be used to trace the metastasis of cancer and research cancer treatment. Further, since it is possible to label genes of various types, the method of the present disclosure can be used to analyze a large number of genes and investigate the diversity of cells in a tissue.

If the method of analysis by an optical marker according to an embodiment of the present disclosure is used, the intensity of reflected light is 10 or more times higher than that of the conventional fluorescence marker, and, thus, detection can be easily made and the stability of maintaining the intensity of the reflected light for a long time is high.

Furthermore, if a sensing material selectively conjugated to an analyte is additionally coated onto the spherical dielectric material, it is possible to selectively target a cell or other samples. If the sensing material is bound, the selectivity for the analyte is increased, and, thus, it becomes easier to label a desired material.

Moreover, the method of analysis by an optical marker of the present disclosure can be applied to a detector capable of detecting a specific protein or a specific molecule.

BRIEF DESCRIPTION OF THE DRAWINGS

FIG. 10 is a graph showing the measured size of the cell aggregate labeled with the reflected light marker according to an example of the present disclosure as time goes by.

DETAILED DESCRIPTION OF THE EMBODIMENTS

Figure 1:
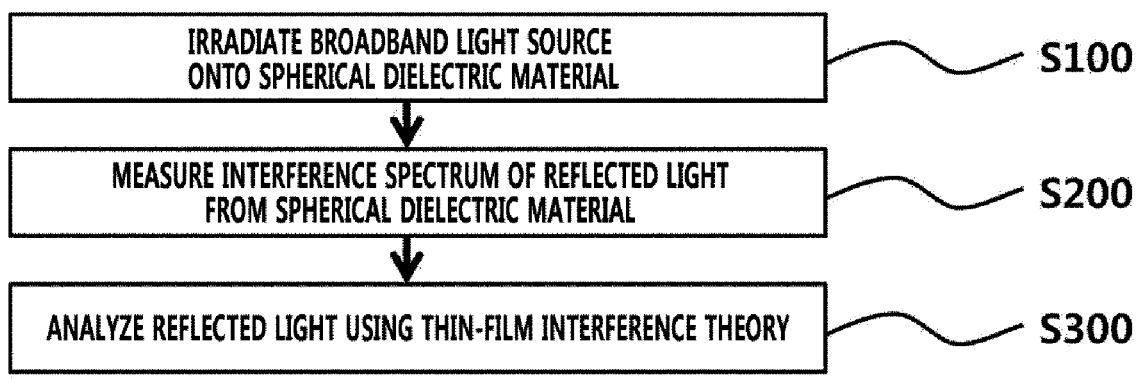
FIG. 1 is a flowchart showing a method of analysis by an optical marker according to an embodiment of the present disclosure.

Hereafter, examples will be described in detail with reference to the accompanying drawings so that the present disclosure may be readily implemented by those skilled in the art.

However, it is to be noted that the present disclosure is not limited to the examples but can be embodied in various other ways. In the drawings, parts irrelevant to the description are omitted for the simplicity of explanation, and like reference numerals denote like parts through the whole document.

Throughout this document, the term "connected to" may be used to designate a connection or coupling of one element to another element and includes both an element being "directly connected" another element and an element being "electronically connected" to another element via another element.

Through the whole document, the terms "on", "above", "on an upper end", "below", "under", and "on a lower end" that are used to designate a position of one element with respect to another element include both a case that the one element is adjacent to the other element and a case that any other element exists between these two elements.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, a marker, a spherical dielectric material, and a probe may be used with the same meaning, but may not be limited thereto.

Hereafter, a method of analysis by an optical marker according to the present disclosure will be described in detail with reference to embodiments, examples, and the accompanying drawings. However, the present disclosure is not limited to the following embodiments, examples, and drawings.

A first aspect of the present disclosure relates to a method of analysis by an optical marker, including: irradiating a broadband light source onto a spherical dielectric material; measuring an interference spectrum of reflected light from the spherical dielectric material; and analyzing the reflected light using the thin-film interference theory.

FIG. 1 is a flowchart showing a method of analysis by an optical marker according to an embodiment of the present disclosure.

First, a broadband light source is irradiated onto a spherical dielectric material (S100).

According to an embodiment of the present disclosure, the spherical dielectric material may have a diameter of from 0.1 μm to 500 μm, but may not be limited thereto.

The spherical shape may be a three-dimensional round shape, but may not be limited thereto.

Assuming sphericity is defined by points at a constant distance from a fixed point, the spherical shape may be a three-dimensional shape having a boundary along the sphericity, but may not be limited thereto.

The spherical dielectric material may be exceptionally in the form of a fabric, but may not be limited thereto.

The fabric may have an aspect ratio of 10 or more, but may not be limited thereto.

According to an embodiment of the present disclosure, the spherical dielectric material may include soft materials including a solid polymer, hydrogel, liposome, and combinations thereof, or gas-based materials including aerogel, but may not be limited thereto.

The spherical dielectric material may include a microbead, but may not be limited thereto.

The microbead may be formed of a dielectric material, but may not be limited thereto.

A subject to be labeled or detected by the method of analysis by the optical marker may be a material selected from the group consisting of cells, proteins, molecules, antibodies, enzymes, quantum dots, viruses, bacteria, and combinations thereof, but may not be limited thereto.

The proteins may include proteins selected from the group consisting of tert-butyl oxycarbonyl(Boc)-diphenylalanine, phenylalanine, tryptophan, tyrosine, leucine, valine, isoleucine, histidine, and combinations thereof, but may not be limited thereto.

According to an embodiment of the present disclosure, the spherical dielectric material may include one material layer or two or more material layers, but may not be limited thereto.

Even if the spherical dielectric material includes one material layer or two or more material layers, the thickness of each material layer of the spherical dielectric material can be seen using the thin-film interference theory according to the following Equation 1 to Equation 4.

According to an embodiment of the present disclosure, the spherical dielectric material may have a surface coated with a material having binding specificity, but may not be limited thereto.

An antigen or antibody is formed on a surface of the spherical dielectric material, and, thus, an antigen or antibody that specifically reacts with the antigen or antibody can be easily detected. That is, the size of the spherical dielectric material can be accurately measured, and, thus, a specific material can be labeled or detected. Further, the spherical dielectric material is coated with the material having binding specificity, and, thus, a desired material can be selectively labeled and detected.

According to an embodiment of the present disclosure, the spherical dielectric material may have stimuli-responsive reactivity and thus may vary in size or internal refractive index depending on chemical or physical conditions, but may not be limited thereto.

According to an embodiment of the present disclosure, the spherical dielectric material may include a spherical dielectric material of multiple layers which are different from each other in thickness or internal refractive index, but may not be limited thereto.

Herein, 20 or more spherical dielectric materials may be analyzed at the same time, but the present disclosure may not be limited thereto.

The spherical dielectric material of multiple layers may be formed of one or more layers, but may not be limited thereto.

Figure 12:
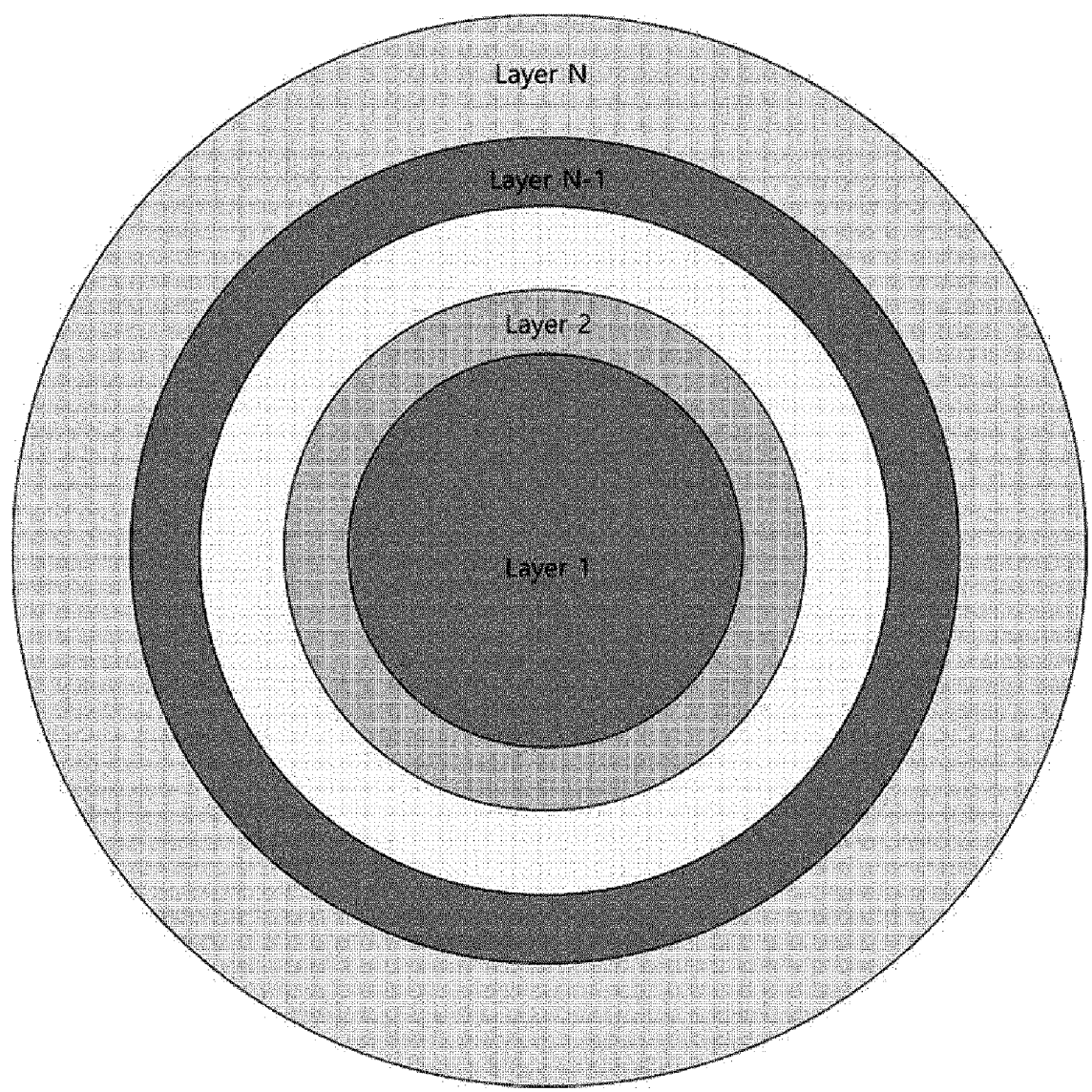
FIG. 12 is a diagram showing a spherical dielectric material of multiple layers according to an embodiment of the present disclosure.

FIG. 12 is a diagram showing a spherical dielectric material of multiple layers according to an embodiment of the present disclosure.

According to an embodiment of the present disclosure, the broadband light source may have a wavelength with a bandwidth of from 20 nm to 2,000 nm, but may not be limited thereto.

As the wavelength of the broadband light source has a broader bandwidth, an analysis can be made accurately and precisely. Therefore, even when the wavelength of the broadband light source has a bandwidth of 2,000 nm or more, the method of analysis by the optical marker can be performed.

The broadband light source may include a light source generated from a light emitting diode (LED), an organic light emitting diode (OLED), a laser, a tungsten lamp, and combinations thereof, but may not be limited thereto.

Then, an interference spectrum of the reflected light from the spherical dielectric material is measured (S200).

The reflected light may be caused by Fresnel reflection of the irradiated broadband light source, but may not be limited thereto.

According to an embodiment of the present disclosure, the measuring of the interference spectrum of the reflected light may be performed by a spectroscope or an acoustic-optic tunable filter, but may not be limited thereto.

According to an embodiment of the present disclosure, the interference spectrum may be measured by selectively collecting only an optical focus signal of reflected light reflected from the center of the spherical dielectric material with a confocal optical system, but may not be limited thereto.

The confocal optical system may include a confocal microscope, but may not be limited thereto.

The confocal optical system may include a phinhole, but may not be limited thereto.

The confocal optical system can receive only light reflected from the focus through the phinhole and thus obtain a clearer image. To be specific, when a sample is observed or measured using the confocal optical system, an incident light source is irradiated to the sample and a light source reflected from the sample passes a photodetector through the phinhole. In this case, a light source reflected from other than the center of the sample (or the center of the microbead) cannot pass the photodetector through the phinhole. Therefore, the phinhole filters the light reflected from other than the center of the sample (or the center of the microbead), and, thus, a clearer image can be obtained.

Figure 2:
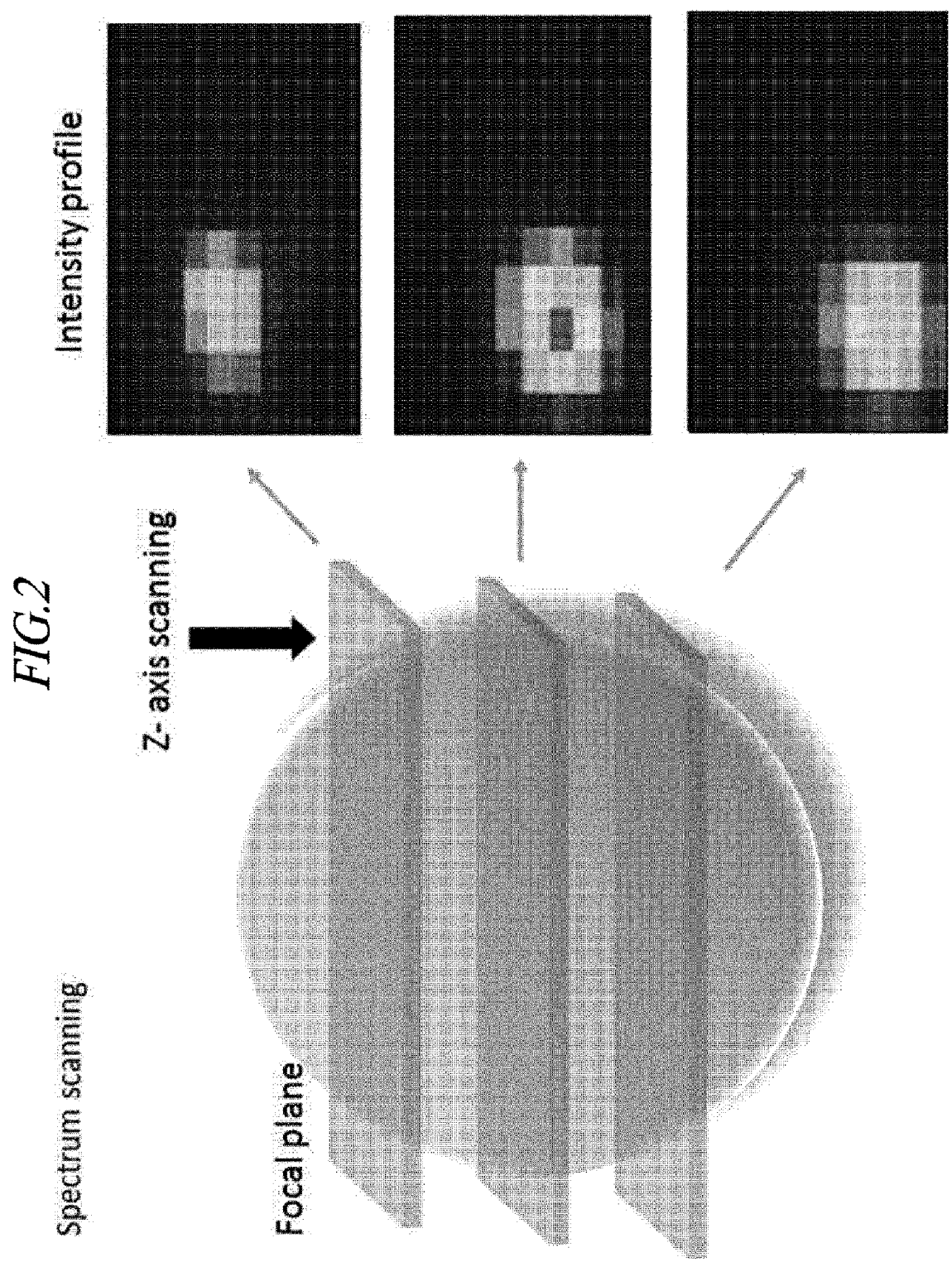
FIG. 2 is a schematic diagram showing a 3D scanning method of a spherical dielectric material according to an example of the present disclosure.

FIG. 2 is a schematic diagram showing a 3D scanning method of a spherical dielectric material according to an example of the present disclosure.

To be specific, the method may further include 3D scanning of the spherical dielectric material with the confocal microscope to find the strongest signal source which is the most strongly reflected among the reflected light, but may not be limited thereto.

A spectrum of the most strongly reflected light source may be represented by 3D scanning with the confocal microscope, but may not be limited thereto.

According to an embodiment of the present disclosure, the method may further include, before the analyzing of the reflected light using the thin-film interference theory, normalizing the broadband light source and the reflected light, but may not be limited thereto.

The normalization may include dividing a value of the spectrum of the irradiated broadband light source by a value of the spectrum of the reflected light. Otherwise, the normalization may include dividing the value of the spectrum of the reflected light by the value of the spectrum of the irradiated light source.

The reflected light may be reflected from an outer surface and/or an inner surface of the spherical dielectric material, but may not be limited thereto.

Interference phenomenon may occur between light reflected from the two different surfaces of the spherical dielectric material. In this case, the optical spectrum may show a periodic pattern with respect to the wavenumber like a sine function or a cosine function.

Then, the reflected light is analyzed using the thin-film interference theory (S300).

According to an embodiment of the present disclosure, the analyzing of the reflected light using the thin-film interference theory may include comparing a function of an analyzed intensity R of the reflected light according to the following Equation 1 to Equation 4 with an actually measured intensity R of the reflected light, but may not be limited thereto.

$$M = \begin{pmatrix} M_{11} & M_{12} \\ M_{21} & M_{22} \end{pmatrix} = J_0^{-1} \left( \prod_{i=1}^{m} H_i \right) J_m \quad \text{[Equation 1]}$$

In the above Equation 1, when the spherical dielectric material is formed of m number of layers, J is represented by the following Equation 2, $$J_i = \begin{pmatrix} s_i & s_i \\ t_i & -t_i \end{pmatrix}, i = 1, \ldots, m+1 \quad \text{[Equation 2]}$$

H is represented by the following Equation 3, and $$H_i = \begin{pmatrix} \cos(k n_i d_i \cos \theta_i) & i \sin(k n_i d_i \cos \theta_i) \frac{s_i}{t_i} \\ i \sin(k n_i d_i \cos \theta_i) \frac{t_i}{s_i} & \cos(k n_i d_i \cos \theta_i) \end{pmatrix}, \quad \text{[Equation 3]}$$

$$i = 1, \ldots, m$$

in the above Equations 1, 2, and 3, $d_i$ represents the thickness of an ith thin film of the spherical dielectric material, $\theta_i$ represents the degree of an incident angle of the broadband light source, $n_i$ represents the refractive index of the ith thin film of the spherical dielectric material, and in a transverse electric field mode, $s_i$ is 1, $t_i$ is $n_i \cos \theta_i$, and k is represented by $$\frac{2\pi}{\lambda},$$

and in a transverse magnetic field, $s_i$ is $\cos \theta_i$ and $t_i$ is $n_i$, but may not be limited thereto.

$$R = \left|\frac{M_{21}}{M_{11}}\right|^2 \qquad \text{[Equation 4]}$$

In the above Equation 4, R represents the intensity of the reflected light.

Herein, k represents the wavenumber.

Equation 1 is a characteristic matrix used to predict an electromagnetic wave after an electromagnetic wave of an incident light source passes through the spherical dielectric material. The characteristic matrix can be represented as $$\begin{bmatrix} E_2 \\ H_2 \end{bmatrix} = \begin{bmatrix} M_{11} & M_{12} \\ M_{21} & M_{22} \end{bmatrix} \begin{bmatrix} E_1 \\ H_1 \end{bmatrix},$$

and $E_1$ and $H_1$ represent an electric field and a magnetic field, respectively, before the electromagnetic wave passes through the dielectric material and $E_2$ and $H_2$ represent an electric field and a magnetic field, respectively, after the electromagnetic wave passes through the dielectric material.

After M of the characteristic matrix is obtained according to the above Equations 1 to 3, the intensity R of reflected light for each wavelength can be obtained according to the above Equation 4 and then compared with a measured value to measure the size of the spherical dielectric material.

To be specific, the intensity R of the reflected light can be represented as a function of wavelength λ or wavenumber k according to the above Equations 1 to 4. For example, referring to FIG. 3B, the normalized intensity of reflected light depending on the wavenumber can be represented as a graph through computer simulation, and the graph is shown differently depending on the diameter of the spherical dielectric material. That is, a theoretical value depending on the diameter of the spherical dielectric material can be obtained according to the above Equations 1 to 4 and a value measured through a test is compared with the theoretical value to analyze the size (diameter) of the spherical dielectric material.

The diameter of the spherical dielectric material may be analyzed according to the following Equations 5 and 6, but may not be limited thereto.

$$R = \frac{r_{01}^2 + r_{12}^2 + 2r_{01}r_{12}\cos 2\delta}{1 + r_{01}^2 r_{12}^2 + 2r_{01}r_{12}\cos 2\delta} \qquad \text{[Equation 5]}$$

In the above Equation 5, R represents the intensity of the reflected light, and $r_{01}$ and $r_{02}$ represent $$r_{01} = \frac{n_0 - n_1}{n_0 + n_1} \text{ and } r_{12} = \frac{n_1 - n_2}{n_1 + n_2},$$

respectively, and $n_0$ and $n_2$ each represent independently a refractive index of a medium around the spherical dielectric material and $n_1$ represents a refractive index of the spherical dielectric material, δ is represented by the following Equation 6, and $$\delta = \frac{2\pi n_1 d}{\lambda} \qquad \text{[Equation 6]}$$

d represents the diameter of the spherical dielectric material and λ represents the wavelength of the irradiated broadband light source, but may not be limited thereto.

The above Equations 5 and 6 are derived using the above Equations 1 to 4.

When the spherical dielectric material is formed of a single layer, the diameter of the spherical dielectric material can be obtained using the above Equations 5 and 6.

That is, when the spherical dielectric material is formed of a single layer, the Equations 5 and 6 can be used to obtain the diameter of the spherical dielectric material more simply than the Equations 1 to 4.

The spherical dielectric material can be analyzed by analyzing the normalized spectrum of the irradiated broadband light source and the reflected light using the above Equation 1 to Equation 6.

The above Equation 1 to Equation 4 are general expressions for thin-film interference and can be used to analyze reflected light generated from all spherical dielectric materials formed of one or more layers.

The above Equations 5 and 6 can be used to analyze reflected light from the spherical dielectric material formed of a single layer.

The size of the spherical dielectric material can be analyzed using the thin-film interference theory, and the presence or absence of a subject to be labeled or detected can be seen based on a change in the size of the spherical dielectric material occurring when the subject to be labeled or detected is adsorbed on the spherical dielectric material. The subject to be labeled or detected can be identified by analyzing the size of the subject to be labeled or detected.

The subject to be labeled or detected can be adsorbed on the spherical dielectric material, and a measured value may vary depending on whether the subject is adsorbed or not. The adsorbed subject to be labeled or detected can be analyzed based on a change in the measured value, which can be applied to a sensor or a marker.

To consider diffraction and polarization of light in addition to the thin-film interference theory, the theory of electromagnetic wave may be used to analyze the spherical dielectric material, but the present disclosure may not be limited thereto.

To be specific, the above Equations 1 to 6 are derived using the theory of electromagnetic wave. In consideration of polarization of light, s and t values may be differently represented in the above Equation 2 depending on the transverse electric field mode or the transverse magnetic field mode.

The spherical dielectric material may be analyzed using the diffraction theory, but may not be limited thereto.

When the spherical dielectric material is analyzed, the size, internal refractive index, specificity, and properties of the dielectric material may be analyzed, but the present disclosure may not be limited thereto.

The size of the spherical dielectric material may be measured with an error of 2 nm or less, but may not be limited thereto.

When the size of the spherical dielectric material is measured repeatedly for analysis, the standard deviation in the measurement is less than 2 nm, which means that the accuracy is high. For this reason, when there are markers different in size up to about 1 μm, the sizes of 20 or more spherical dielectric materials can be analyzed at the same time. Further, when the sizes of spherical dielectric materials with a difference in size of more than 1 μm are analyzed, thousands or more of the spherical dielectric materials can be analyzed at the same time. The conventional fluorescence marker has the disadvantage that it can label only 3 to 5 subjects at the same time. The method of the present disclosure is a method to overcome the disadvantage of the conventional fluorescence marker. Since it is possible to analyze multiple subjects at the same time, it is possible to trace and observe individual cells in a cell aggregate. Particularly, the method of the present disclosure can be used to trace the metastasis of cancer and research cancer treatment. Further, since it is possible to label genes of various types, the method of the present disclosure can be used to analyze a large number of genes and investigate the diversity of cells in a tissue.

If the method of analysis by an optical marker is used, the intensity of reflected light is 10 or more times higher than that of the conventional fluorescence marker, and, thus, detection can be easily made and the stability of maintaining the intensity of the reflected light for a long time is high.

Furthermore, if a sensing material selectively conjugated to an analyte is additionally coated onto the spherical dielectric material, it is possible to selectively label a cell or other samples. If the sensing material is bound, the selectivity for the analyte is increased, and, thus, it becomes easier to label a desired material.

The sensing material may be a material with specificity, but may not be limited thereto.

Moreover, the method of analysis by an optical marker of the present disclosure can be applied to a detector capable of detecting a specific protein or a specific molecule.

Hereafter, the present disclosure will be described in more detail with reference to examples. The following examples are provided only for explanation, but do not intend to limit the scope of the present disclosure.

Example

First, to find the most strongly reflected light when white light was irradiated to a microbead used as a spherical dielectric material, the microbead was 3D-scanned using a confocal microscope. A spectrum of incident light and a spectrum of reflected light at a portion where the strongest light was reflected was obtained from the 3D scanning result. Normalization was carried out by dividing the spectrum of the reflected light by the spectrum of the incident light. The normalized spectrum was analyzed to measure the size of the microbead using the following Equation 5, and the microbead to which the white light was irradiated was referred to as a reflected light marker.

$$R = \frac{r_{01}^2 + r_{12}^2 + 2r_{01}r_{12}\cos 2\delta}{1 + r_{01}^2 r_{12}^2 + 2r_{01}r_{12}\cos 2\delta} \quad \text{[Equation 5]}$$

In the above Equation 5, R represents the intensity of the reflected light, and $r_{01}$ and $r_{02}$ represent $$r_{01} = \frac{n_0 - n_1}{n_0 + n_1} \text{ and } r_{12} = \frac{n_1 - n_2}{n_1 + n_2},$$

respectively, and $n_0$ and $n_2$ each represent independently a refractive index of a medium around the microbead and $n_1$ represents a refractive index of the microbead, δ is represented by the following Equation 6, and $$\delta = \frac{2\pi n_1 d}{\lambda} \quad \text{[Equation 6]}$$

d represents the diameter of the microbead and λ represents the wavelength of the irradiated broadband light source.

Test Example

Characteristics of the reflected light marker prepared according to Example were checked, and a result thereof was as shown in FIG. 3 and FIG. 4.

Figure 3A:
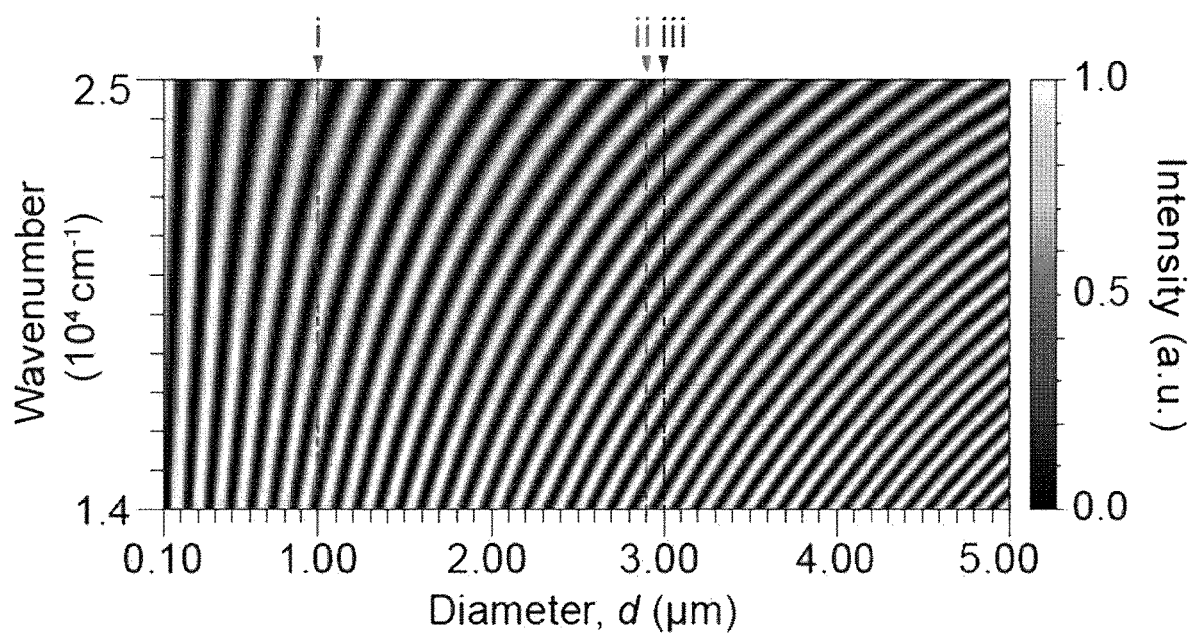
FIG. 3A is a 2D graph of reflection spectra from microbeads with a size of from 1 μm to 5 μm according to an example of the present disclosure.
Figure 3B:
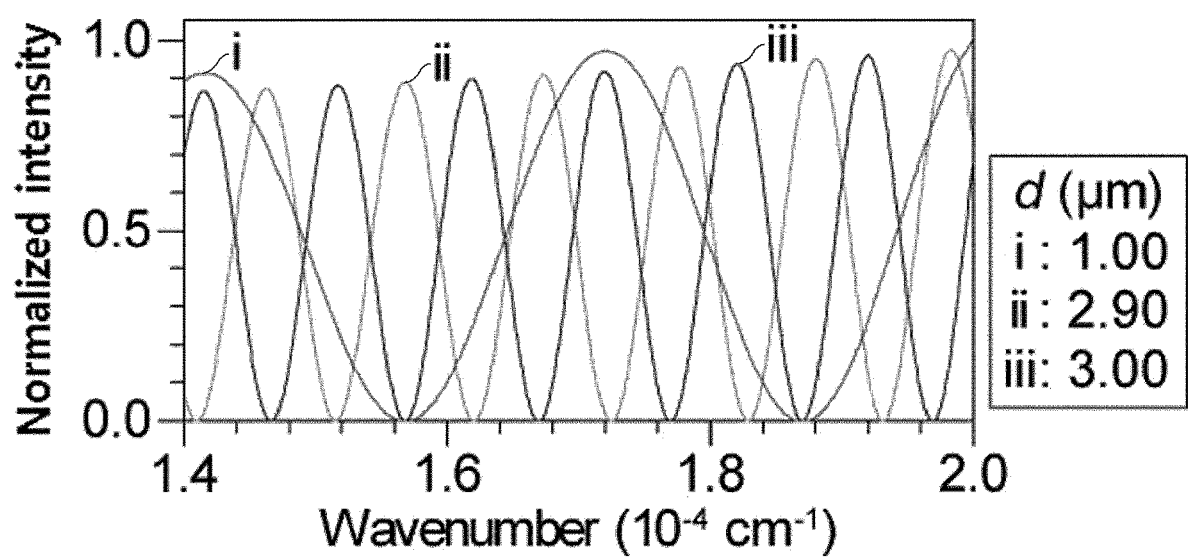
FIG. 3B is a graph of reflection spectra from three microbeads in the graph shown in FIG. 3A.

FIG. 3A is a 2D graph of reflection spectra from microbeads with a size of from 0.1 μm to 5 μm according to an example of the present disclosure, and FIG. 3B is a graph of reflection spectra from three microbeads in the graph shown in FIG. 3A.

To be specific, the graphs shown in FIG. 3A and FIG. 3B show the normalized intensity of reflected light depending on the wavenumber for each size of the microbead using the above Equations 5 and 6.

Figure 4A:
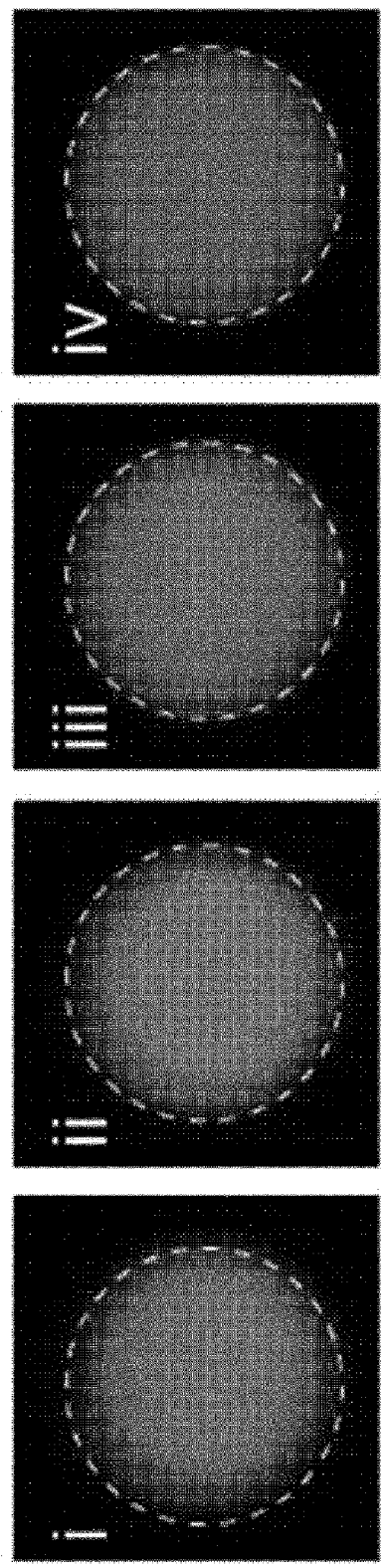
FIG. 4A shows fluorescent images of a microbead dyed with a fluorescence marker according to a comparative example.
Figure 4B:
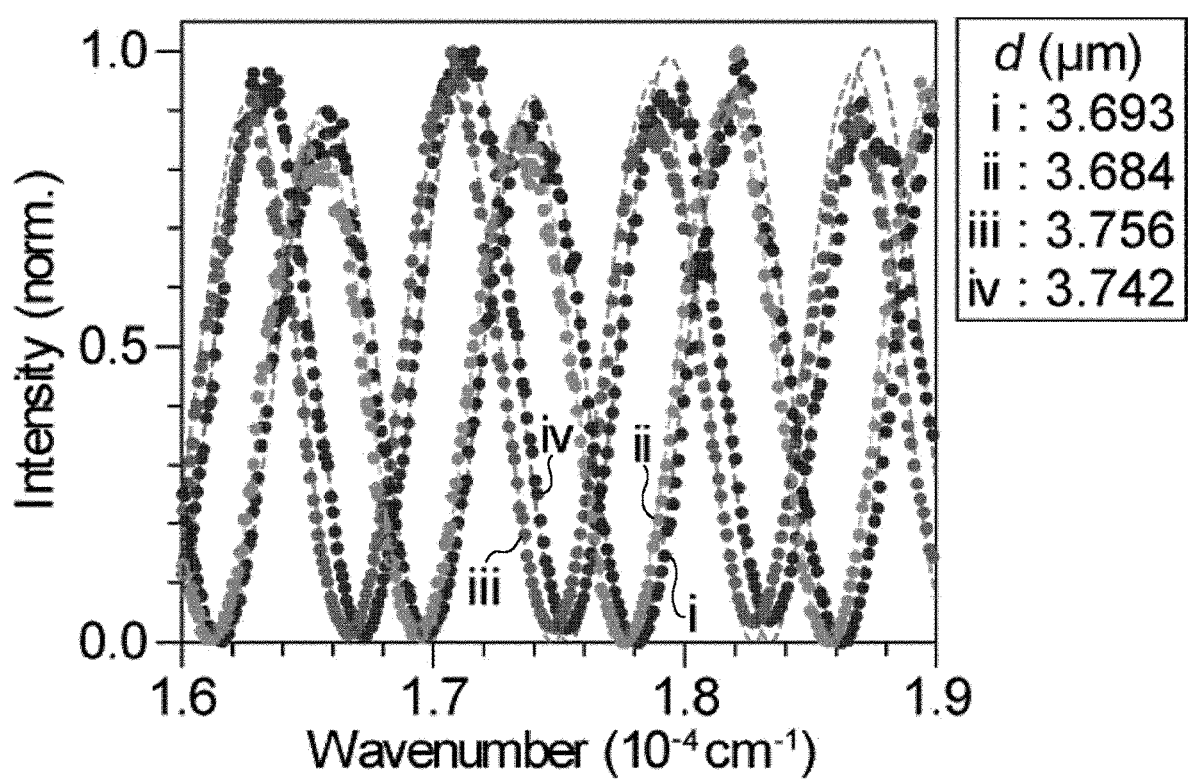
FIG. 4B shows a spectrum of a reflected light marker according to an example of the present disclosure.
Figure 4C:
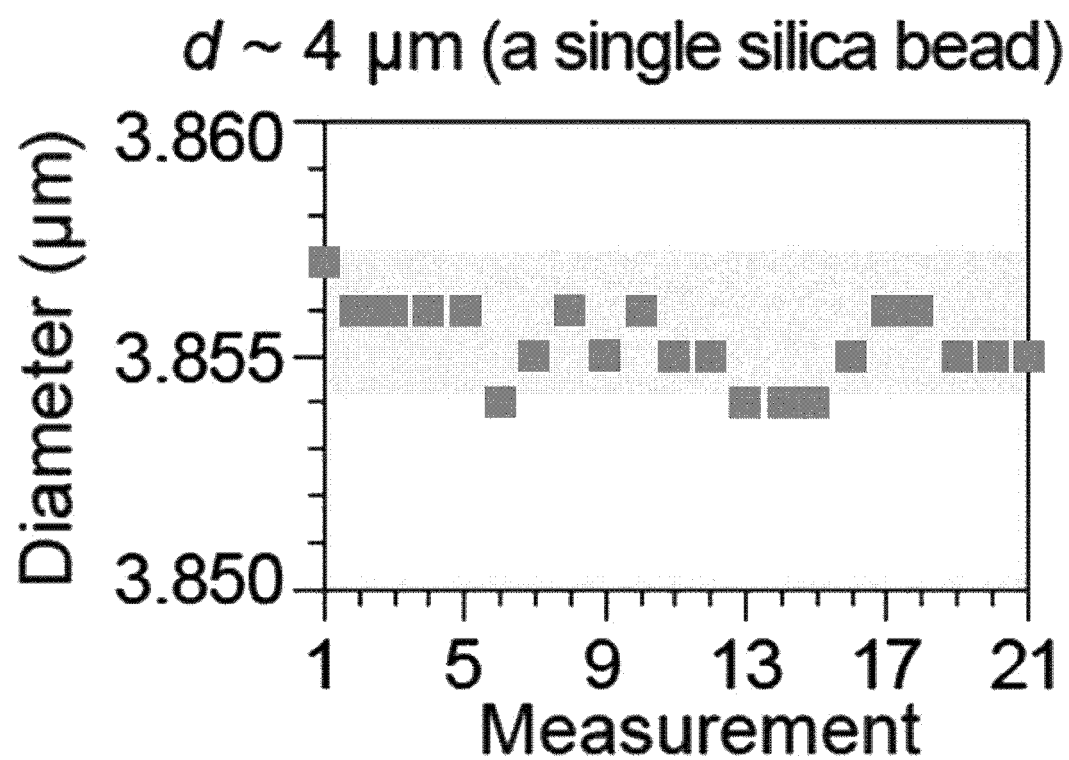
FIG. 4C shows the size of the reflected light marker depending on the number of times of measurement when the size of the reflected light marker according to an example of the present disclosure is measured repeatedly.
Figure 4D:
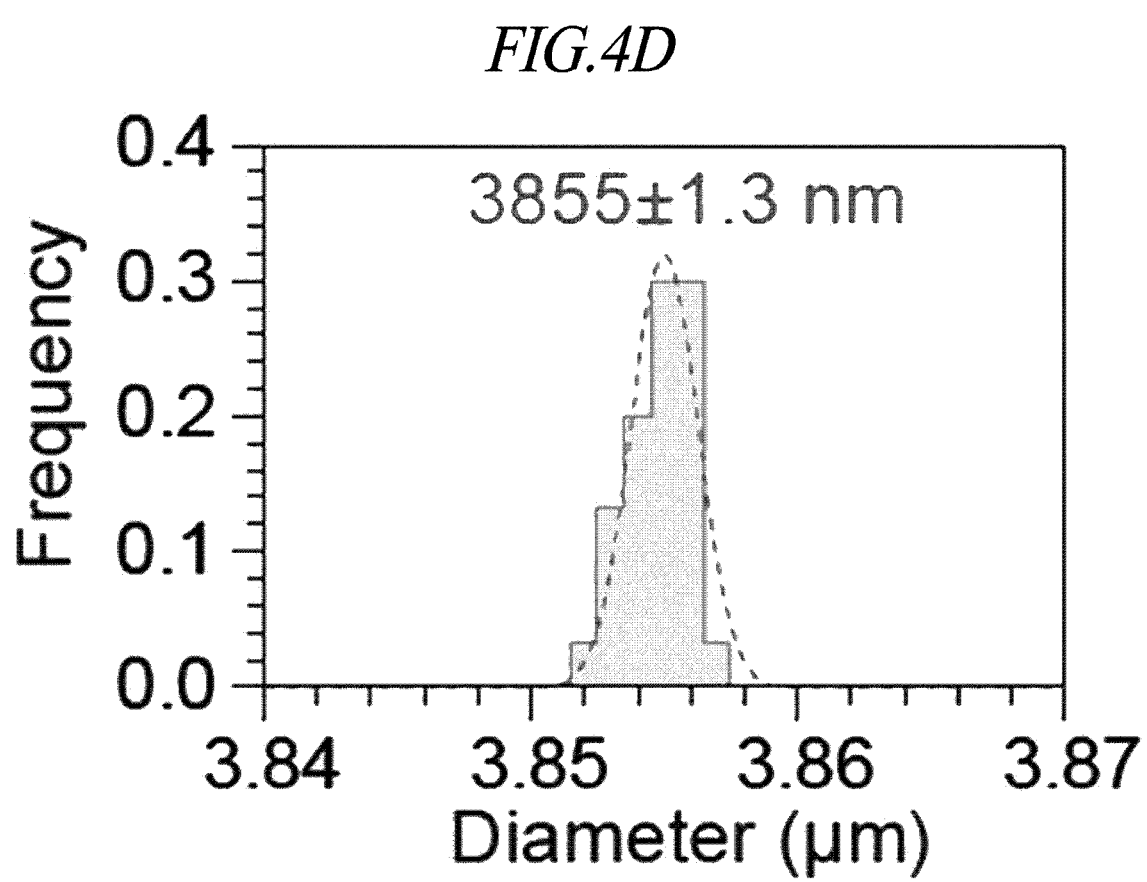
FIG. 4D is a graph showing the standard deviation of the sizes of the reflected light marker shown in FIG. 4C.

FIG. 4A shows fluorescent images of a microbead dyed with a fluorescence marker according to a comparative example, FIG. 4B shows a spectrum of a reflected light marker according to an example of the present disclosure, FIG. 4C shows the size of the reflected light marker depending on the number of times of measurement when the size of the reflected light marker according to an example of the present disclosure is measured repeatedly, and FIG. 4D is a graph showing the standard deviation of the sizes of the reflected light marker shown in FIG. 4C.

To be specific, FIG. 4A and FIG. 4B show the comparison between the conventional fluorescence marker and the technology of the present disclosure. In the fluorescent images of the microbead dyed with the fluorescence marker as shown in FIG. 4A, it is difficult to compare the sizes of the microbead. However, by comparing and analyzing the graph of the intensity of reflected light depending on the wavenumber of the reflected light marker shown in FIG. 4B with the graphs showing the result values obtained using the above Equations 5 and 6 as shown in FIG. 3A and FIG. 3B, it can be seen that the size of a microbead i is 3.693 μm, the size of a microbead ii is 3.684 μm, the size of a microbead iii is 3.756 μm, and the size of a microbead iv is 3.742 μm. FIG. 4C is a graph showing the size of the microbead depending on the number of times of measurement when the reflected light marker was measured repeatedly, and the measurement error was up to 1.5 nm. The standard deviation shown in FIG. 4D is 1.3 nm, which confirms that the degree of accuracy is very high. Thus, 20 or more micromaterials can be measured and analyzed at the same time.

Figure 5:
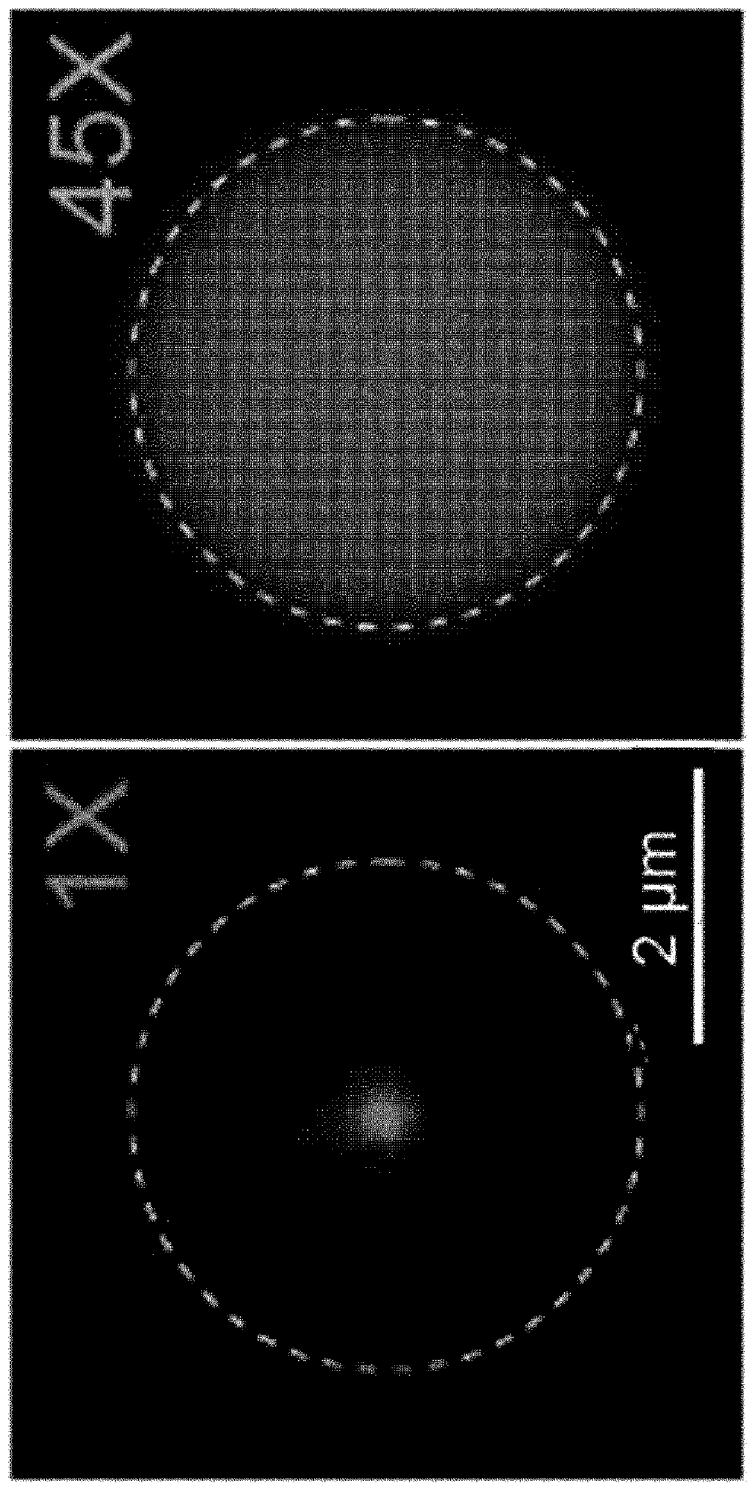
FIG. 5 shows an image of a reflected light marker according to an example of the present disclosure and an image of a fluorescence marker according to a comparative example.
Figure 6:
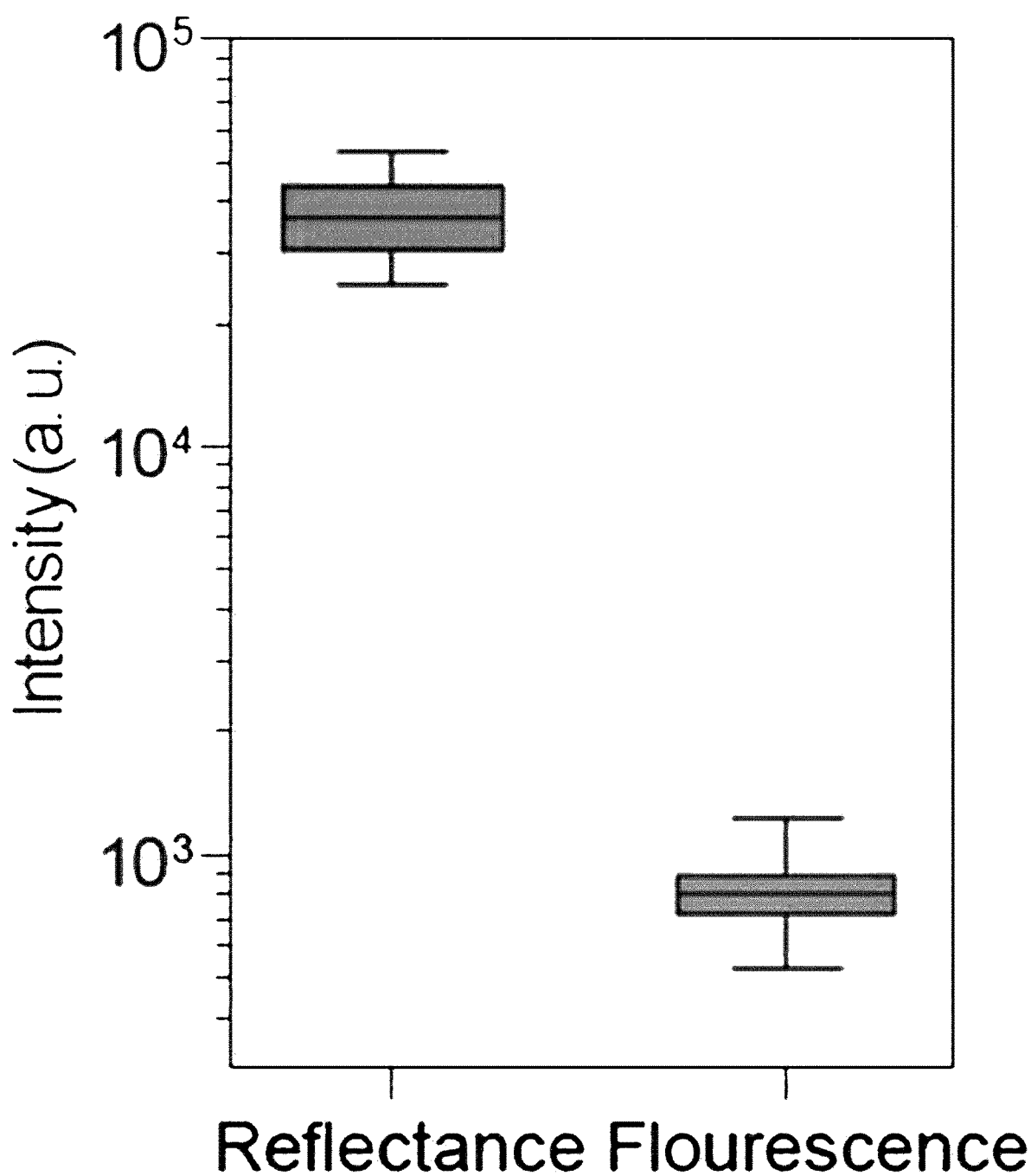
FIG. 6 is a graph showing the intensity of the reflected light marker according to an example of the present disclosure and the intensity of the fluorescence marker according to a comparative example.
Figure 7:
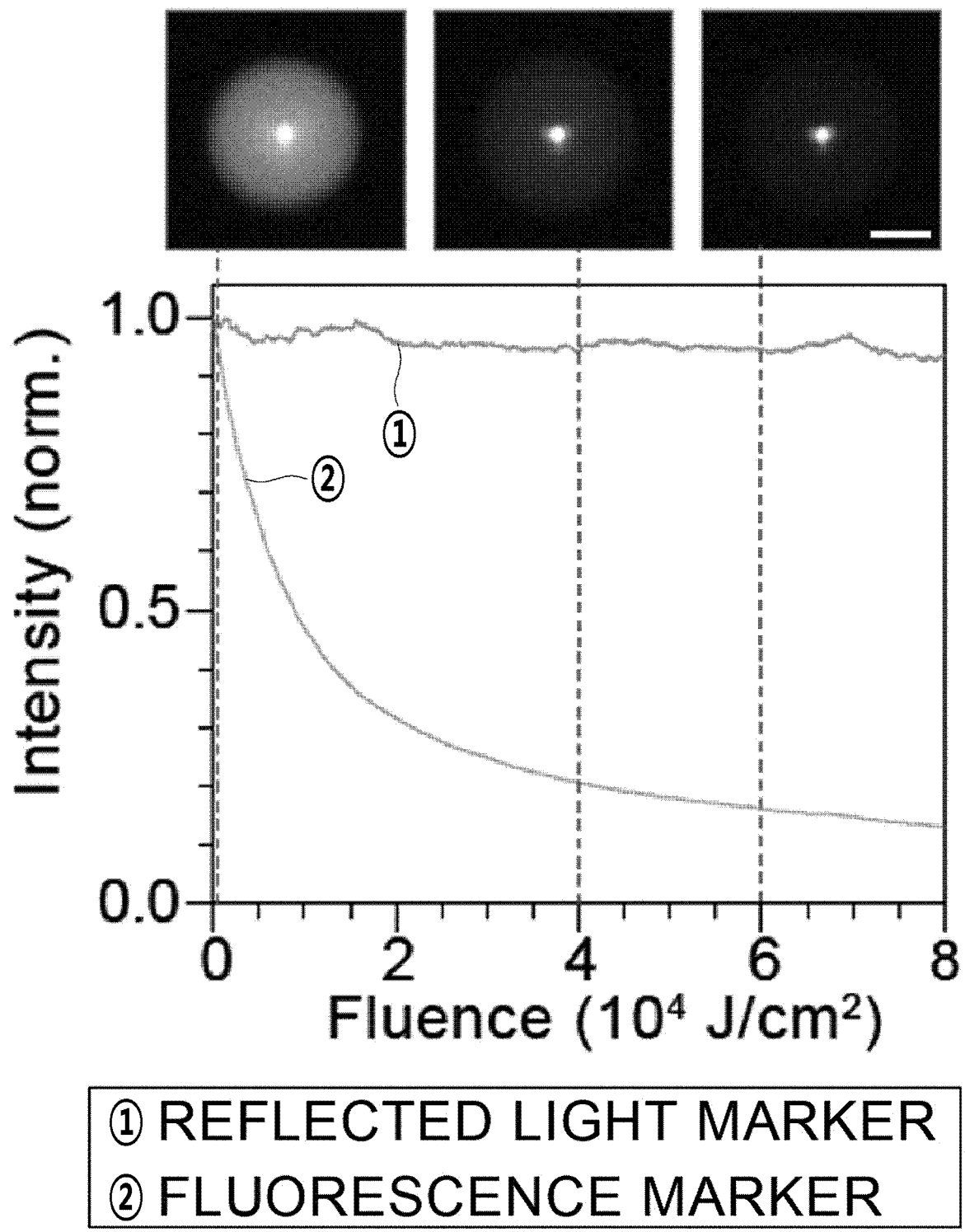
FIG. 7 is a graph showing the intensity of a signal from of the reflected light marker according to an example of the present disclosure and the fluorescence marker according to a comparative example when light is continuously given.

The intensity and stability of a signal from of the reflected light marker prepared according to Example were checked and compared with the intensity and stability of a signal according to the method using the conventional fluorescence marker as a comparative example, and a result thereof was as shown in FIG. 5 to FIG. 7.

FIG. 5 shows an image of a reflected light marker according to an example of the present disclosure and an image of a fluorescence marker according to a comparative example.

According to the result shown in FIG. 5, the reflected light marker according to an example of the present disclosure as can be seen from the left of FIG. 5 showed a strong light signal at the center. Further, the fluorescence marker according to a comparative example as can be seen from the right of FIG. 5 showed a weak light signal, and, thus, the light signal could be detected when adjusted to be 45 times brighter than the initial brightness.

FIG. 6 is a graph showing the intensity of the reflected light marker according to an example of the present disclosure and the intensity of the fluorescence marker according to a comparative example.

According to the result shown in FIG. 6, by comparison between the intensities of the reflected light marker and the fluorescence marker, it can be seen that the intensity of light from the reflected light marker was 10 or more times higher than the intensity of light from the fluorescence marker.

The reflected light marker according to an example of the present disclosure exhibits a higher intensity of light than the conventional fluorescence marker, and, thus, it is easily detected.

FIG. 7 is a graph showing the intensity of a signal from of the reflected light marker according to an example of the present disclosure and the fluorescence marker according to a comparative example when light is continuously given.

According to the result shown in FIG. 7, it can be seen that when light was continuously given, the reflected light marker exhibited a constant intensity of light, whereas the fluorescence marker exhibited a gradually decreasing intensity of light.

Therefore, it was confirmed that the reflected light marker according to an example of the present disclosure has a high stability.

Figure 8:
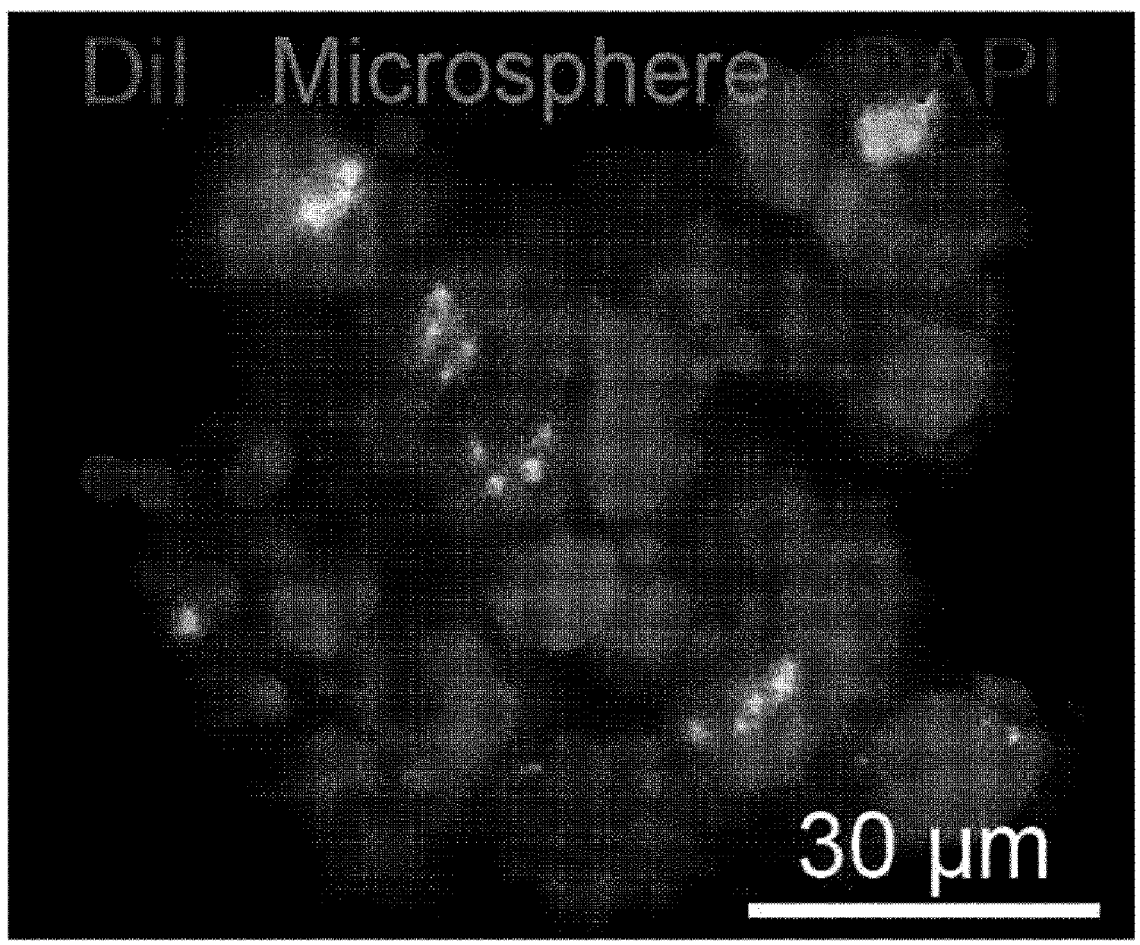
FIG. 8 is an image of a cell aggregate labeled with the reflected light marker according to an example of the present disclosure.
Figure 9:
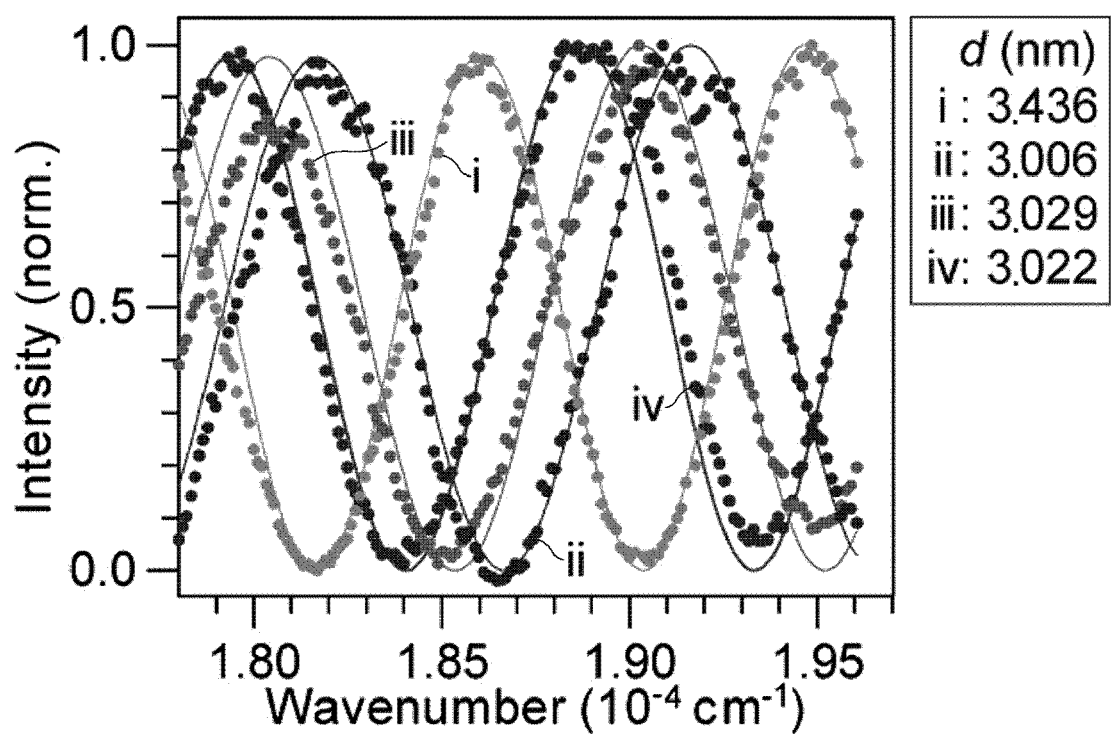
FIG. 9 is a graph showing spectra of the cell aggregate labeled with the reflected light marker according to an example of the present disclosure as the intensity depending on the wavenumber.

Cell tracking characteristics of the reflected light marker prepared according to Example were checked, and a result thereof was as shown in FIG. 8 and FIG. 9.

FIG. 8 is an image of a cell aggregate labeled with the reflected light marker according to an example of the present disclosure.

To be specific, in FIG. 8, a portion labeled in red is a cell membrane, a portion labeled in purple is a cell nucleus, and a portion labeled in blue is a reflected light marker.

FIG. 9 is a graph showing spectra of the cell aggregate labeled with the reflected light marker according to an example of the present disclosure as the intensity depending on the wavenumber.

According to the result shown in FIG. 9, it can be seen that a spectrum signal from the reflected light marker according to an example of the present disclosure can be readily measured even in a cell tissue in which scattering often occurs.

Figure 10:
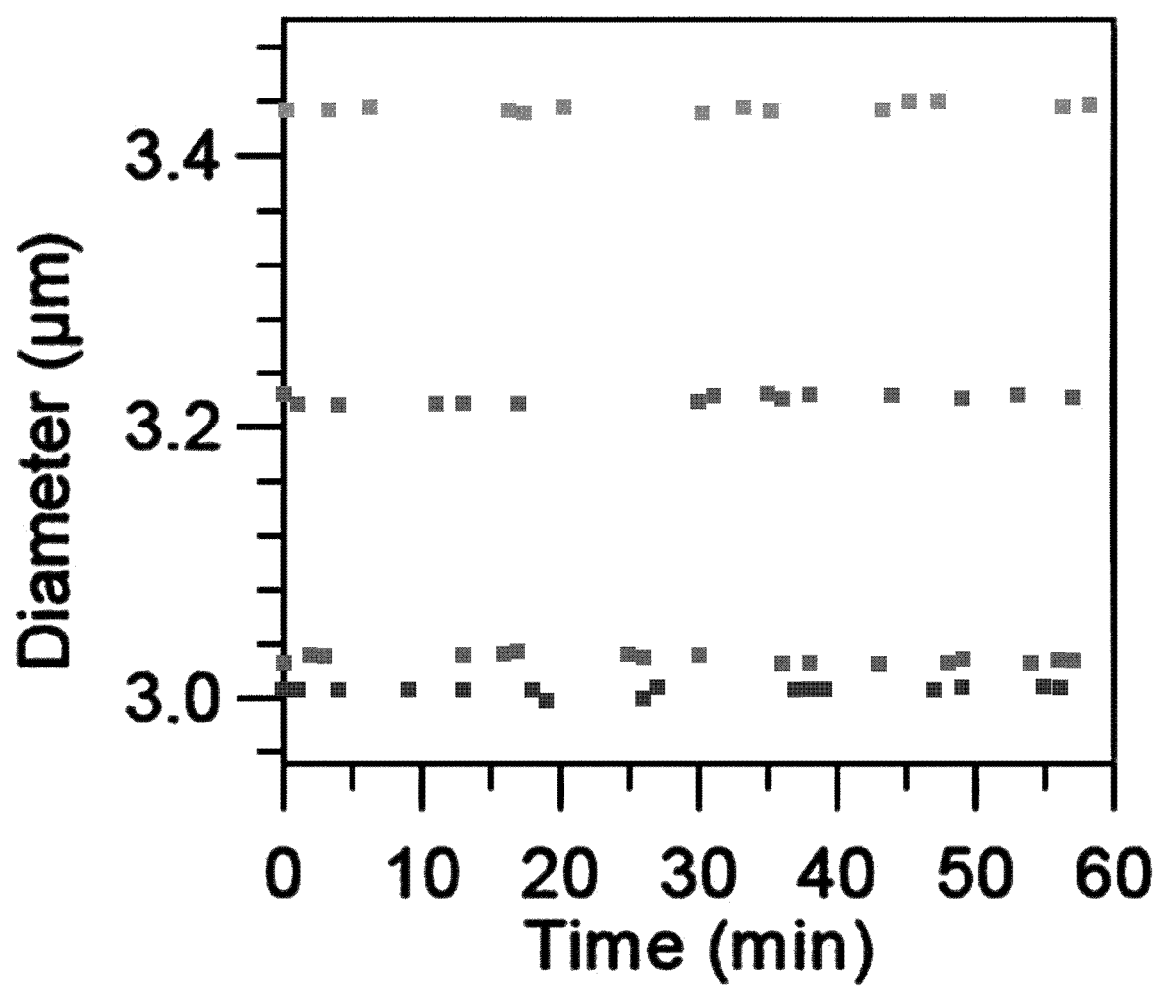

FIG. 10 is a graph showing the measured size of the cell aggregate labeled with the reflected light marker according to an example of the present disclosure as time goes by.

According to the result shown in FIG. 10, it can be seen that the reflected light marker can be readily traced with an accuracy of ±3 nm for 1 hour.

Figure 11:
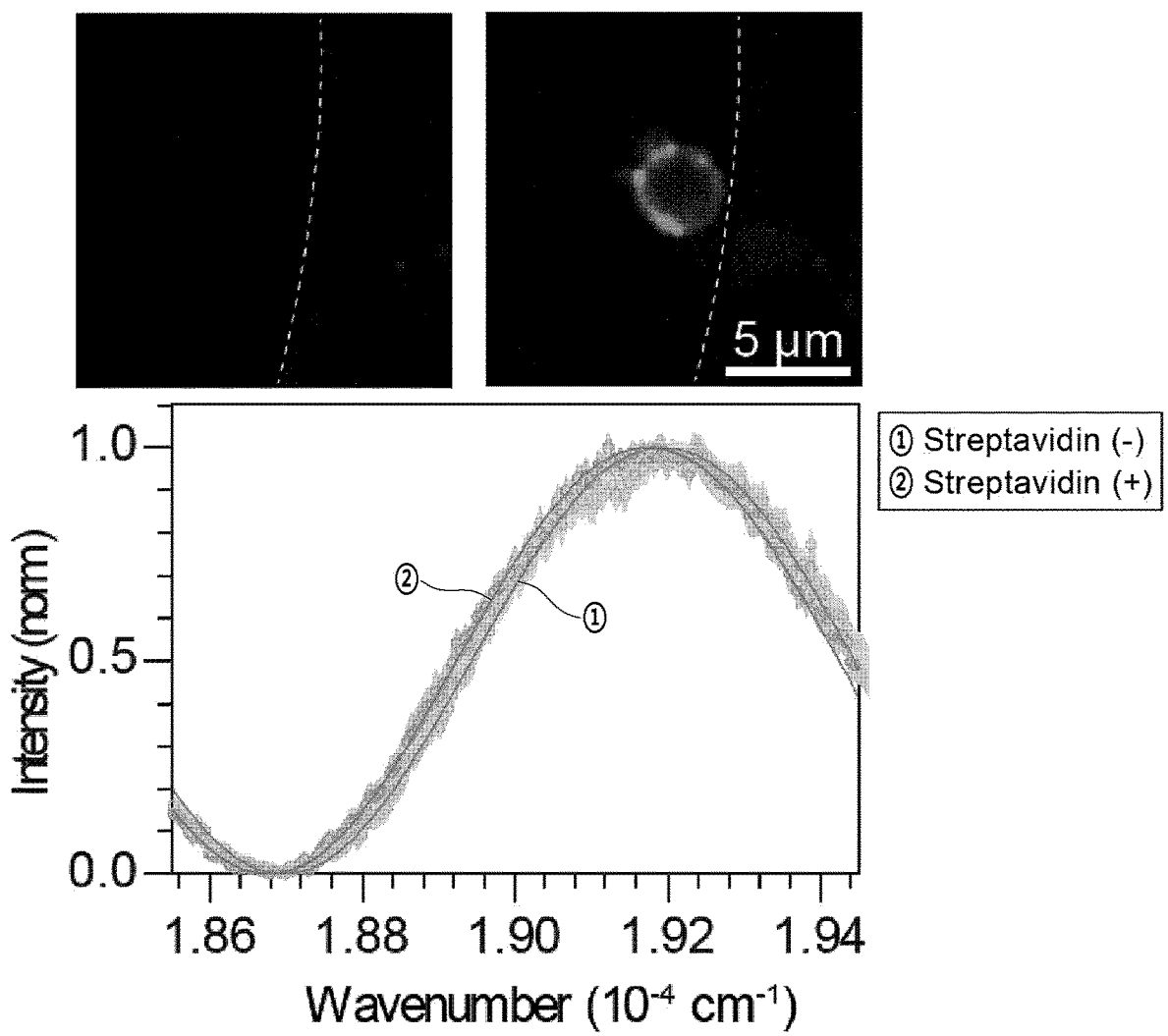
FIG. 11 provides images and spectra showing a change when a molecule to be detected is adsorbed on the reflected light marker according to an example of the present disclosure.

Molecule detection characteristics of the reflected light marker prepared according to Example were checked, and a result thereof was as shown in FIG. 11.

FIG. 11 provides images and spectra showing a change when a molecule to be detected is adsorbed on the reflected light marker according to an example of the present disclosure.

According to the result shown in FIG. 11, it can be seen that when a fluorescence-labeled streptavidin molecule was adsorbed onto the reflected light marker, a phase of a reflected light spectrum was changed. Thus, it is confirmed that the reflected light marker can be applied as a molecule detector.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A method of analysis by an optical marker, comprising:
irradiating a broadband light source onto a spherical dielectric material;
measuring an interference spectrum of reflected light from the spherical dielectric material; and
analyzing the reflected light using the thin-film interference theory.

2. The method of analysis by an optical marker of claim 1, further comprising:
before the analyzing of the reflected light using the thin-film interference theory, normalizing the broadband light source and the reflected light.

3. The method of analysis by an optical marker of claim 1, wherein the analyzing of the reflected light using the thin-film interference theory includes comparing a function of an analyzed intensity R of the reflected light according to the following Equation 1 to Equation 4 with an actually measured intensity R of the reflected light:

$$M = \begin{pmatrix} M_{11} & M_{12} \\ M_{21} & M_{22} \end{pmatrix} = J_0^{-1} \left( \prod_{i=1}^{m} H_i \right) J_m \quad \text{[Equation 1]}$$

(in the above Equation 1, when the spherical dielectric material is formed of m number of layers,
J is represented by the following Equation 2, $$J_i = \begin{pmatrix} s_i & s_i \\ t_i & -t_i \end{pmatrix}, \quad i = 1, \ldots, m+1 \quad \text{[Equation 2]}$$

H is represented by the following Equation 3, $$H_i = \begin{pmatrix} \cos(kn_i d_i \cos\theta_i) & i\sin(kn_i d_i \cos\theta_i)\frac{s_i}{t_i} \\ i\sin(kn_i d_i \cos\theta_i)\frac{t_i}{s_i} & \cos(kn_i d_i \cos\theta_i) \end{pmatrix}, \quad \text{[Equation 3]}$$

$$i = 1, \ldots, m$$

in the above Equations 1, 2, and 3,
$d_i$ represents the thickness of an ith thin film of the spherical dielectric material, $\theta_i$ represents the degree of an incident angle of the broadband light source, $n_i$ represents the refractive index of the ith thin film of the spherical dielectric material, k is represented by $$\frac{2\pi}{\lambda},$$

and in a transverse electric field mode, $s_i$ is 1 and $t_i$ is $n_i \cos \theta_i$, and in a transverse magnetic field, $s_i$ is $\cos \theta_i$ and $t_i$ is $n_i$, and $$R = \left|\frac{M_{21}}{M_{11}}\right|^2 \qquad \text{[Equation 4]}$$

in the above Equation 4,

R represents the intensity of the reflected light).

4. The method of analysis by an optical marker of claim 1, further comprising:

irradiating an optical focus of the broadband light source to the center of the spherical dielectric material.

5. The method of analysis by an optical marker of claim 1, wherein the spherical dielectric material has a diameter of from 0.1 μm to 500 μm.

6. The method of analysis by an optical marker of claim 1, wherein the spherical dielectric material includes soft materials including a solid polymer, hydrogel, liposome, and combinations thereof, or gas-based materials including aerogel.

7. The method of analysis by an optical marker of claim 1, wherein the spherical dielectric material includes one material layer or two or more material layers.

8. The method of analysis by an optical marker of claim 1, wherein the spherical dielectric material has a surface coated with a material having binding specificity.

9. The method of analysis by an optical marker of claim 1, wherein the spherical dielectric material has stimuli-responsive reactivity and thus varies in size or internal refractive index depending on chemical or physical conditions.

10. The method of analysis by an optical marker of claim 1, wherein the spherical dielectric material includes a spherical dielectric material of multiple layers which are different from each other in thickness or internal refractive index.

11. The method of analysis by an optical marker of claim 1, wherein the broadband light source has a wavelength with a bandwidth of from 20 nm to 2,000 nm.

12. The method of analysis by an optical marker of claim 1, wherein the measuring of the interference spectrum of the reflected light is performed by a spectroscope or an acoustic-optic tunable filter.

13. The method of analysis by an optical marker of claim 1, wherein the interference spectrum is be measured by selectively collecting only an optical focus signal of reflected light reflected from the center of the spherical dielectric material with a confocal optical system.

\* \* \* \* \*